(12) United States Patent
Uchiyama et al.

(10) Patent No.: US 8,758,691 B2
(45) Date of Patent: Jun. 24, 2014

(54) HYDROGEN-ABSORBING ALLOY AND HYDROGEN SENSOR USING THE ALLOY

(75) Inventors: Naoki Uchiyama, Hamamatsu (JP);
Tomomi Kanai, Hamamatsu (JP);
Kazumi Harada, Hamamatsu (JP)

(73) Assignee: Kabushiki Kaisha Atsumitec, Shizuoka (JP)

( * ) Notice: Subject to any disclaimer, the term of this patent is extended or adjusted under 35 U.S.C. 154(b) by 0 days.

(21) Appl. No.: 13/641,373

(22) PCT Filed: Feb. 21, 2011

(86) PCT No.: PCT/JP2011/053677
§ 371 (c)(1),
(2), (4) Date: Oct. 15, 2012

(87) PCT Pub. No.: WO2011/129148
PCT Pub. Date: Oct. 20, 2011

(65) Prior Publication Data
US 2013/0028791 A1    Jan. 31, 2013

(30) Foreign Application Priority Data

Apr. 14, 2010    (JP) .................. 2010-093135

(51) Int. Cl.
*G01N 33/22*    (2006.01)
*G01N 21/00*    (2006.01)
*G01N 21/29*    (2006.01)
*G01N 21/59*    (2006.01)

(52) U.S. Cl.
CPC ............... *G01N 21/29* (2013.01); *G01N 21/00* (2013.01); *G01N 21/59* (2013.01)

USPC ............ 422/91; 422/83; 422/94; 436/139; 436/144; 73/23.2

(58) Field of Classification Search
CPC .................. G01N 21/00; G01N 21/29
USPC ........... 422/83, 91, 94; 436/144, 139; 73/23.2
See application file for complete search history.

(56) References Cited

U.S. PATENT DOCUMENTS

| 7,404,842 | B1 * | 7/2008 | Wainright et al. .............. 75/351 |
| 2005/0170946 | A1 * | 8/2005 | Ovshinsky et al. ............. 502/60 |
| 2005/0186117 | A1 * | 8/2005 | Uchiyama et al. ............. 422/91 |

FOREIGN PATENT DOCUMENTS

| EP | 2 154 528 | 2/2010 |
| JP | 10-259436 | 9/1998 |

(Continued)

OTHER PUBLICATIONS

Zhang et al. "The Study on the Electrochemical Performance of Mechanically Alloyed Mg-Ti-Ni-based Ternary and Quaternary Hydrogen Storage Electrode Alloys", International Journal of Hydrogen Energy, Elsevier Science Publishers B.V., vol. 26, No. 8, Aug. 2001, pp. 801-806.

(Continued)

*Primary Examiner* — Lyle Alexander
(74) *Attorney, Agent, or Firm* — Cozen O'Connor

(57) ABSTRACT

A hydrogen sensor using a hydrogen-absorbing alloy containing an Mg—Ni-based alloy and a Zr—Ti-based alloy includes a substrate (2), a hydrogen reaction layer (3) formed on the substrate (2) and containing the Mg—Ni-based alloy and the Zr—Ti-based alloy, and a first catalyst layer (4) formed on the hydrogen reaction layer (3) and capable of accelerating hydrogenation of the Mg—Ni-based alloy.

5 Claims, 4 Drawing Sheets

(56) References Cited

FOREIGN PATENT DOCUMENTS

JP 2004-346418 12/2004
JP 2008-298724 12/2008

OTHER PUBLICATIONS

Anik et al. "Improvement of the Electrochemical Hydrogen Storage Performance of Mg2Ni by the Partial Replacements of Mg by Al, Ti and Zr", Journal of Alloys and Compounds, vol. 486, No. 1-2, Nov. 3, 2009, pp. 109-117.

Bao, et al. "Titanium-Buffer-Layer-Inserted Switchable Mirror Based on MgNi Alloy Thin Film", Japanese Journal of Applied Physics, The Japan Society of Applied Physics, Japan Society of Applied Physics, Tokyo, vol. 45, No. 23, Jan. 1, 2006, pp. L588-L590.

Pasturel et al. "Stabilized Switchable Black State in Mg2NiH4/Ti/Pd Thin Films for Optical Hydrogen Sensing", Applied Physics Letters, American Institute of Physics, vol. 89, No. 2, Jul. 12, 2006, pp. 21913-021913.

* cited by examiner

HYDROGEN-ABSORBING ALLOY AND HYDROGEN SENSOR USING THE ALLOY

RELATED APPLICATIONS

This is a U.S. National Phase Application under 35 USC 371 of International Application PCT/JP2011/053677 filed on Feb. 21, 2011.

This application claims the priority of JP 2010-093135 filed Apr. 14, 2010, the entire content of which is hereby incorporated by reference.

TECHNICAL FIELD

The present invention relates to a hydrogen-absorbing alloy capable of absorbing hydrogen, and a hydrogen sensor using the hydrogen-absorbing alloy to detect hydrogen gas in an atmosphere.

BACKGROUND ART

A hydrogen-absorbing alloy is disclosed in Patent Document 1. As stated in Patent Document 1, when using a fuel cell as an electric power supply for driving a device, it is essential that hydrogen, which is a fuel for the fuel cell, should be handled with care. As a method of safely handling hydrogen, it is especially preferable that hydrogen be absorbed in hydrogen-absorbing alloys, and study has been made on such hydrogen-absorbing alloys. As such alloys, alloys containing Mg and Ni are used, as described in Patent Document 1.

On the other hand, a hydrogen sensor utilizing the characteristics of a hydrogen-absorbing alloy has been developed, wherein a thin layer (thin film) of magnesium-nickel alloy or the like having a light control function is formed on a surface of a substrate made of glass, acrylic resin or the like, and the thin layer is hydrogenated (property of the thin layer is changed) quickly by the action of a catalyst layer (catalyst film) containing palladium or the like. The hydrogen sensor detects change in optical reflectance (hereinafter referred to merely as "reflectance" or, where appropriate, as "optical transmittance") accompanying the hydrogenation of the thin layer, to thereby detect hydrogen gas leaked into an atmosphere. Also, since the thin layer is hydrogenated in a reversible fashion at normal temperature, a hydrogen gas leak can be safely and quickly detected.

No matter whether the hydrogen-absorbing alloy is used in an electric power supply or in a hydrogen sensor, there has been a demand for hydrogen-absorbing alloys of which the required time from the absorption of hydrogen, or hydrogenation, to the desorption of hydrogen, or dehydrogenation, is shorter, in order to improve the performance of the electric power supply or hydrogen sensor. In the application of hydrogen-absorbing alloys to hydrogen sensors in particular, there has been a demand for hydrogen-absorbing alloys that enable a hydrogen sensor to be used repeatedly at short intervals of time so that after the detection of hydrogen at one location, the hydrogen sensor can be used in a short while at a different location to detect the presence of hydrogen. However, the hydrogen-absorbing alloy disclosed in Patent Document 1 and many of similar hydrogen-absorbing alloys reported so far are intended to improve the hydrogen absorption capacity or the handleability and are not intended to shorten the time required to complete the desorption of hydrogen, or dehydrogenation.

PRIOR ART DOCUMENT

Patent Document

Patent Document 1: Japanese Laid-open Patent Publication No. 2004-346418

SUMMARY OF THE INVENTION

Problems to be Solved by the Invention

An object of the present invention is to provide a hydrogen-absorbing alloy capable of quick hydrogen desorption or dehydrogenation after absorbing hydrogen or being hydrogenated, and a hydrogen sensor using the hydrogen-absorbing alloy.

Means for Solving the Problems

The present invention provides a hydrogen-absorbing alloy containing an Mg—Ni-based alloy and a Zr—Ti-based alloy.

Preferably, the hydrogen-absorbing alloy consists essentially of an Mg—Ni alloy and a Zr—Ti—Mn alloy.

The present invention also provides a hydrogen sensor using the hydrogen-absorbing alloy and comprising: a substrate; a hydrogen reaction layer formed on the substrate and containing the Mg—Ni-based alloy and the Zr—Ti-based alloy; and a first catalyst layer formed on the hydrogen reaction layer and capable of accelerating hydrogenation of the Mg—Ni-based alloy.

Preferably, the hydrogen reaction layer is a disperse mixture of the Mg—Ni-based alloy and the Zr—Ti-based alloy.

The hydrogen reaction layer preferably includes a light control layer formed of the Mg—Ni-based alloy, and a second catalyst layer formed of the Zr—Ti-based alloy and capable of accelerating dehydrogenation of the Mg—Ni-based alloy.

Preferably, the second catalyst layer is sandwiched between the light control layer and the substrate.

Preferably, the second catalyst layer is sandwiched between the light control layer and the first catalyst layer.

Preferably, the second catalyst layer is sandwiched between the light control layer and the first catalyst layer and between the light control layer and the substrate.

Advantageous Effects of the Invention

The hydrogen-absorbing alloy of the present invention contains the Zr—Ti-based alloy, and therefore, the hydrogen absorbed in the Mg—Ni-based alloy can be quickly released. That is, dehydrogenation can be expedited.

It was experimentally confirmed that with the combination of the Mg—Ni alloy and the Zr—Ti—Mn alloy according to the present invention, dehydrogenation could be quickly completed.

According to the present invention, the Mg—Ni-based alloy and the Zr—Ti-based alloy are used to form the hydrogen reaction layer that reacts with hydrogen. Accordingly, the hydrogen absorbed in the Mg—Ni-based alloy can be quickly released, that is, dehydrogenation can be speeded up. Hydrogen detecting operation using the hydrogen sensor can therefore be quickly performed.

Also, according to the present invention, the hydrogen reaction layer may be a disperse mixture of the Mg—Ni-based alloy and the Zr—Ti-based alloy, and also in this case, the hydrogen absorbed in the Mg—Ni-based alloy can be quickly released, that is, dehydrogenation can be accelerated.

Hydrogen detecting operation using the hydrogen sensor can therefore be performed without delay.

Further, according to the present invention, the hydrogen reaction layer may include the light control layer formed of the Mg—Ni-based alloy and the second catalyst layer formed of the Zr—Ti-based alloy. The Zr—Ti-based alloy is used to form the second catalyst layer in order to accelerate dehydrogenation of the Mg—Ni-based alloy. As a consequence, the hydrogen absorbed in the light control layer can be quickly desorbed by the second catalyst layer, that is, dehydrogenation can be speeded up. Hydrogen detecting operation using the hydrogen sensor can therefore be carried out quickly.

According to the present invention, the second catalyst layer may be sandwiched between the light control layer and the substrate, and it was experimentally confirmed that also with this configuration, dehydrogenation could be quickly completed.

Further, according to the present invention, the second catalyst layer may alternatively be sandwiched between the light control layer and the first catalyst layer, and it was experimentally ascertained that also with this configuration, dehydrogenation could be quickly completed. The second catalyst layer also serves as a buffer layer for preventing the light control layer from precipitating on the surface of the first catalyst layer as the light control layer is repeatedly expanded and contracted due to hydrogenation and dehydrogenation. This configuration is preferred from the standpoint of preventing oxidation of Mg, because Mg is readily oxidized.

According to the present invention, moreover, the second catalyst layer not only permits the light control layer to be quickly dehydrogenated but also prevents the light control layer from entering the first catalyst layer and precipitating on its surface due to repeated hydrogenation and dehydrogenation.

MODE FOR CARRYING OUT THE INVENTION

Figure 1:
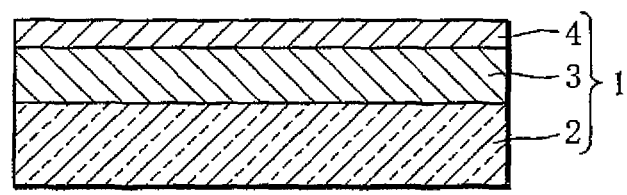
FIG. 1 is a schematic diagram of a hydrogen sensor according to the present invention.

As illustrated in FIG. 1, a hydrogen sensor 1 according to the present invention includes a substrate 2, a hydrogen reaction layer 3, and a first catalyst layer 4.

The substrate 2 is a transparent plate member such as an acrylic plate, a plastic plate, a transparent sheet, or a glass plate.

The hydrogen reaction layer 3 contains an Mg—Ni-based alloy as well as a Zr—Ti-based alloy. An Mg—Ni-based alloy is a material capable of absorbing and desorbing hydrogen and switchable between a transparent state and a mirror state (metallic state) or an intermediate state. Instead of the Mg—Ni-based alloy, a thin film of a rare earth element such as yttrium, lanthanum or the like, a thin film of a rare earth metal-magnesium alloy, a thin film of a magnesium-transition metal alloy, or a thin film of magnesium may be used. The Mg—Ni-based alloy is especially preferable because of its low material cost and excellent optical characteristics. The hydrogen reaction layer 3 is deposited on the substrate 2. The deposition may be carried out by sputtering, vacuum vapor deposition, electron beam evaporation, chemical vapor deposition (CVD), plating or the like.

For the first catalyst layer 4, palladium or the like is used. The first catalyst layer 4 is deposited on the surface of the hydrogen reaction layer 3, and the deposition may be executed by sputtering, vacuum vapor deposition, electron beam evaporation, chemical vapor deposition (CVD), plating or the like.

The hydrogen sensor configured as described above is capable of measuring hydrogen. Specifically, when the hydrogen sensor is exposed to an atmosphere containing hydrogen, hydrogenation (hydrogen absorption) of the hydrogen reaction layer 3 takes place, so that the state of the hydrogen reaction layer 3 changes from the metallic state to the transparent state. On the other hand, when the hydrogen sensor is exposed to an atmosphere not containing hydrogen and containing oxygen, dehydrogenation (hydrogen desorption) takes place and the state of the hydrogen reaction layer 3 changes from the transparent state to the metallic state.

The Mg—Ni-based alloy and the Zr—Ti-based alloy are contained in the hydrogen reaction layer 3, as stated above, and constitute a hydrogen-absorbing alloy of the present invention. Hydrogen absorption and desorption mainly take place in the Mg—Ni-based alloy, and by additionally containing the Zr—Ti-based alloy, it is possible to quickly desorb the hydrogen absorbed in the Mg—Ni-based alloy, that is, to speed up the dehydrogenation. Especially, where the hydrogen reaction layer 3 is formed using only an Mg—Ni alloy and a Zr—Ti—Mn alloy as described later, the dehydrogenation can be significantly accelerated, as confirmed by experimentation.

The hydrogen sensors 1 illustrated in FIGS. 1 to 4 use the hydrogen-absorbing alloy as their hydrogen reaction layer 3. In the hydrogen sensor 1 of FIG. 1, the hydrogen reaction layer 3 is formed by dispersively mixing an Mg—Ni alloy and a Zr—Ti—Mn alloy (Example 1). The dispersive mixing is carried out in the manner described below. First, the substrate 2 is washed and then set in a vacuum apparatus for evacuation. Subsequently, co-sputtering of Mg—Ni and Zr—Ti—Mn targets is executed for one minute. Specifically, direct current sputtering is performed with power of 100 W applied to the Mg—Ni target and with power of 30 W applied to the Zr—Ti—Mn target.

Figure 2:
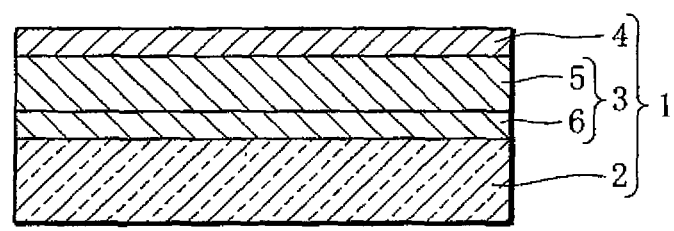
FIG. 2 is a schematic diagram of another hydrogen sensor according to the present invention.
Figure 3:
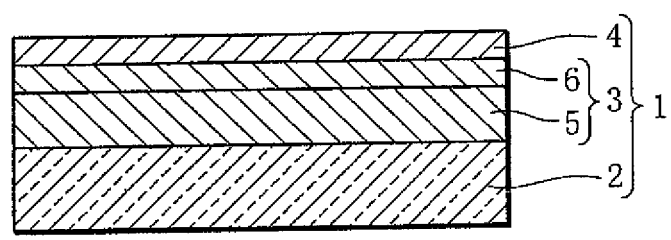
FIG. 3 is a schematic diagram of still another hydrogen sensor according to the present invention.
Figure 4:
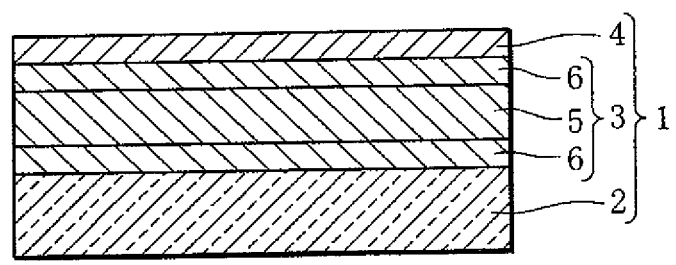
FIG. 4 is a schematic diagram of yet another hydrogen sensor according to the present invention.

In the hydrogen sensor of FIG. 2, the Mg—Ni alloy and the Zr—Ti—Mn alloy are used to form separate layers. Specifically, the Mg—Ni alloy is used to form a light control layer 5, and the Zr—Ti—Mn alloy is used to form a second catalyst layer 6. The light control layer 5 and the second catalyst layer 6 constitute the hydrogen reaction layer 3. In the hydrogen sensor of FIG. 2, the second catalyst layer 6 is sandwiched between the light control layer 5 and the substrate 2 (Example 2). In the hydrogen sensor illustrated in FIG. 3, the second catalyst layer 6 is sandwiched between the light control layer 5 and the first catalyst layer 4 (Example 3). In the hydrogen sensor illustrated in FIG. 4, the second catalyst layer 6 is sandwiched between the light control layer 5 and the first catalyst layer 4 and between the light control layer 5 and the substrate 2 (Example 4). That is, the hydrogen sensor of FIG. 4 has two second catalyst layers 6 sandwiching the light control layer 5 therebetween. In this manner, the hydrogen sensor may have a desired configuration insofar as the Mg—Ni alloy and the Zr—Ti—Mn alloy are disposed between the substrate 2 and the first catalyst layer 4.

In the following, the results of experiments conducted on the hydrogen sensors 1 of the present invention will be explained. Using, as a comparative example, a hydrogen sensor in which only the Mg—Ni alloy is disposed between the substrate 2 and the first catalyst layer 4, experiments were conducted on the hydrogen sensors 1 of the present invention and the comparative example with a view to comparing the time required for dehydrogenation.

Figure 5:
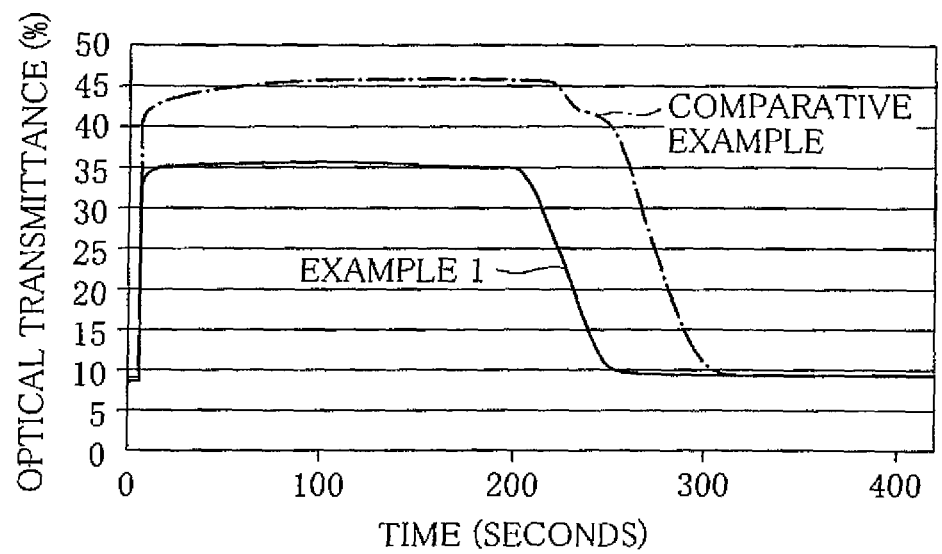
FIG. 5 is a graph showing hydrogen desorption characteristics of Example 1.

FIG. 5 is a graph showing the result of comparison between Example 1 and the comparative example, wherein the vertical axis indicates the transmittance (%) of light and the horizontal axis indicates the time elapsed after the supply of hydrogen. To supply hydrogen, 100% hydrogen was supplied at a flow rate of 50 ml/min. In the graph, the solid line indicates Example 1, and the dot-dash line indicates the comparative example. As shown in the graph, as soon as the supply of hydrogen is started, the transmittance of light sharply rises, so that the degree of transparency rises. After a lapse of a predetermined time, dehydrogenation begins, and the transmittance of light returns to the original level. It can be said that the earlier the transmittance of light returns to the original level, the shorter time the dehydrogenation requires. In the comparative example, the dehydrogenation requires about 300 seconds; in Example 1, the dehydrogenation is completed in about 250 seconds. That is to say, the hydrogen sensor in which the hydrogen reaction layer 3 formed by dispersively mixing the Mg—Ni alloy and the Zr—Ti—Mn alloy is sandwiched between the substrate 2 and the first catalyst layer 4 is dehydrogenated quicker than the hydrogen sensor in which only the Mg—Ni alloy is used to form the hydrogen reaction layer 3. In the hydrogen sensors used for the experiments, the thickness of the first catalyst layer 4 was set to 4 nm, and the thickness of the hydrogen reaction layer 3 was set to 22.3 nm. The volume ratio of the Mg—Ni alloy to the Zr—Ti—Mn alloy in the hydrogen reaction layer 3 was about 10:1. The Mg—Ni alloy and the Zr—Ti—Mn alloy were dispersively mixed by being subjected to co-sputtering for one minute. Even with the hydrogen reaction layer 3 obtained by dispersively mixing the Mg—Ni-based alloy and the Zr—Ti-based alloy, the hydrogen absorbed in the Mg—Ni-based alloy can be quickly desorbed, namely, the dehydrogenation can be speeded up. Hydrogen detecting operation with the use of the hydrogen sensor can therefore be quickly performed. In the graph, Example 1 shows a lower transmittance of light than the comparative example. Although the transmittance of light is somewhat low, no problem arises so far as the transparency of the hydrogen sensor can be perceived by the naked eye. The optical transmittance of Example 1 is about 35%, which poses no problem in practical use.

Figure 6:
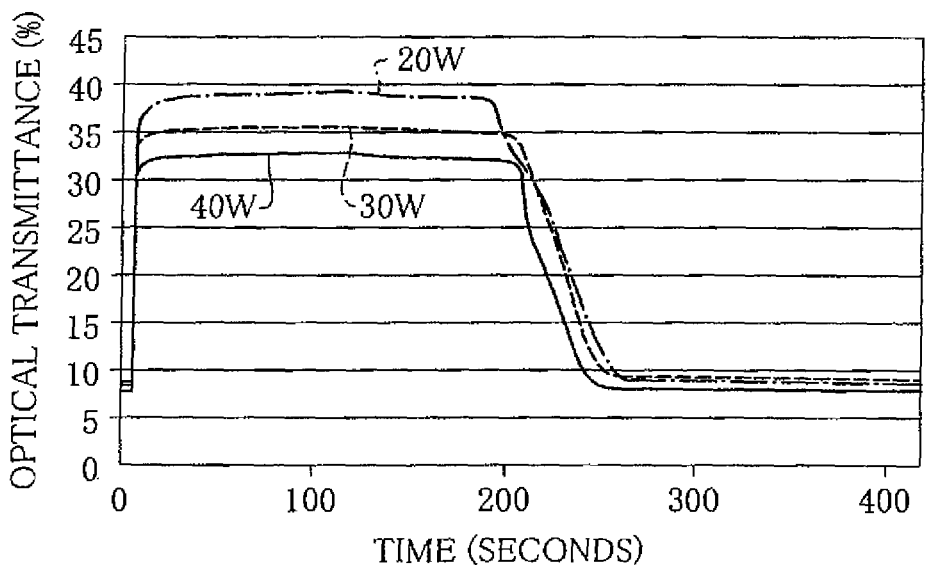
FIG. 6 is a graph also showing hydrogen desorption characteristics of Example 1.
Figure 7:
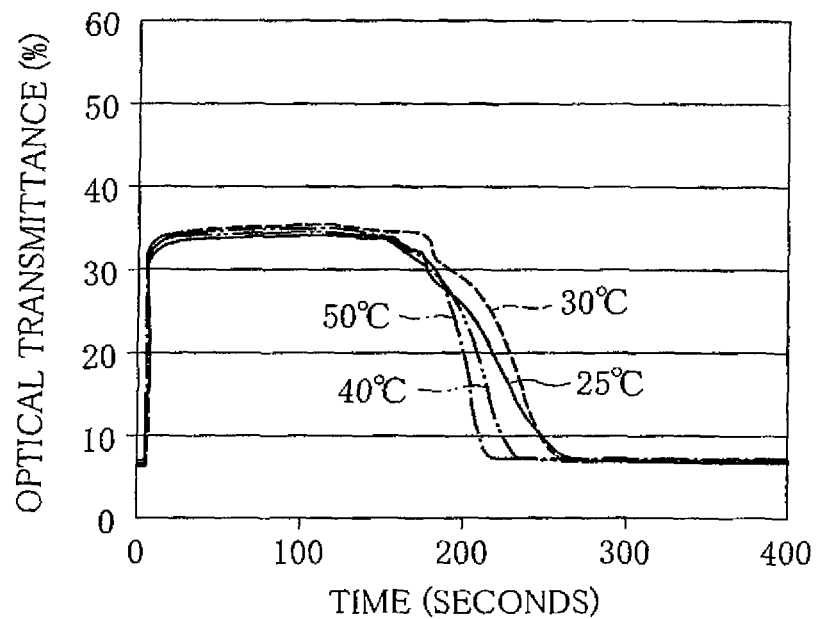
FIG. 7 is a graph showing hydrogen desorption characteristics of Example 1.

It was also experimentally confirmed that the dehydrogenation could be expedited by increasing the content of the Zr—Ti—Mn alloy (increasing the power (W) applied to the Zr—Ti—Mn target during the co-sputtering), as shown in FIG. 6. As shown in the graph, in all examples, the dehydrogenation is completed in about 250 seconds. It was confirmed that this effect was observed when the volume ratio of the Mg—Ni alloy to the Zr—Ti—Mn alloy was at least in the range of 10:0.5 to 10:2.0. Further, it was also experimentally ascertained that the time required for the dehydrogenation could be shortened by raising ambient temperature, as shown in FIG. 7. As shown in the graph, in all examples, the dehydrogenation is completed in about 250 seconds. It was confirmed that the effect could be observed when the ambient temperature was at least in the range of 25° C. to 50° C.

Figure 8:
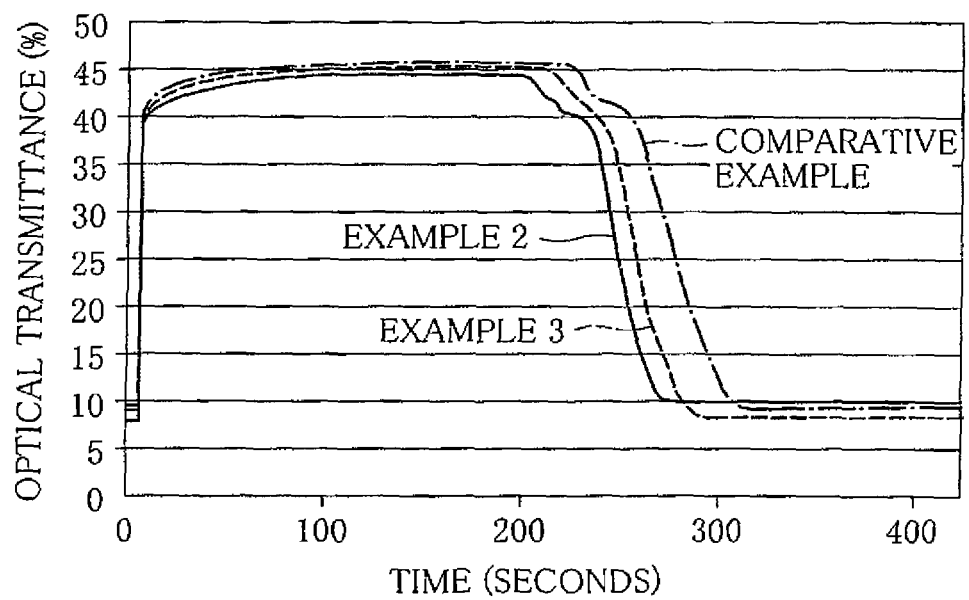
FIG. 8 is a graph showing hydrogen desorption characteristics of Examples 2 and 3.

FIG. 8 is a graph showing the results of comparison of Examples 2 and 3 with the comparative example. In the graph, the solid line indicates Example 2, the broken line indicates Example 3, and the dot-dash line indicates the comparative example. As shown in the graph, the examples and the comparative example exhibit similar transmittances of light. The dehydrogenation is completed in about 270 seconds in the case of Example 2, in about 280 seconds in the case of Example 3, and in about 300 seconds in the case of the comparative example. That is, with the hydrogen sensors in which the light control layer of the Mg—Ni-based alloy and the second catalyst layer of the Zr—Ti-based alloy are formed separately and sandwiched between the substrate and the first catalyst layer, the hydrogen absorbed in the light control layer can be desorbed more quickly. In other words, the dehydrogenation can be speeded up. Accordingly, the hydrogen detecting operation with the use of the hydrogen sensor can be repeated at short intervals of time. In the hydrogen sensors used for the experiments, the thickness of the first catalyst layer 4 was set to 4 nm, the thickness of the light control layer 5 was set to 20 nm, and the thickness of the second catalyst layer 6 was set to 1 nm. Similar experimental results were obtained also with respect to the hydrogen sensor with the second catalyst layer 6 having a thickness of 2 nm, though not illustrated. As stated above, it was experimentally confirmed that with the hydrogen sensor having the second catalyst layer sandwiched between the light control layer and the substrate, the dehydrogenation could be speeded up. In addition, it was experimentally ascertained that the dehydrogenation could be expedited also with respect to the hydrogen sensor having the second catalyst layer sandwiched between the light control layer and the first catalyst layer. Where the second catalyst layer is sandwiched between the light control layer and the first catalyst layer, the second catalyst layer serves as a buffer layer for preventing the light control layer from precipitating on the surface of the first catalyst layer as the light control layer is repeatedly expanded and contracted due to hydrogenation and dehydrogenation. Since Mg is readily oxidized, in particular, it is preferable from the standpoint of preventing oxidation of Mg that the second catalyst layer be sandwiched between the light control layer and the first catalyst layer. In the other respects, the experiments were conducted in the same manner as explained with reference to FIG. 5.

With Example 4, the advantageous effects of both Examples 2 and 3 can be obtained. That is, the time required for the dehydrogenation can be shortened, compared with the comparative example, and also the effect of the buffer layer is available.

From the experimental results explained above, it is clear that the use of the Zr—Ti—Mn alloy serves to speed up the dehydrogenation. In particular, Example 1 shows the best results in terms of the dehydrogenation.

The hydrogen sensor 1 of the present invention can be used for other purposes than hydrogen detection, for example, as a screen for privacy protection, an ornament, a toy and the like that utilize the switching function of the light control layer 5 between the mirror state and the transparent state.

EXPLANATION OF REFERENCE SIGNS 1 hydrogen sensor
2 substrate
3 hydrogen reaction layer
4 first catalyst layer
5 light control layer
6 second catalyst layer

The invention claimed is:
1. A hydrogen sensor comprising:
a substrate;
a hydrogen reaction layer formed on the substrate and containing a Mg—Ni-based alloy and a Zr—Ti-based alloy; and a first catalyst layer laminated on the hydrogen reaction layer so as to cover an entire surface of the hydrogen reaction layer and being capable of accelerating hydrogenation of the Mg—Ni-based alloy, wherein the hydrogen reaction layer comprises a light control layer formed of the Mg—Ni-based alloy, and a second catalyst layer formed of the Zr—Ti-based alloy and being capable of accelerating dehydrogenation of the Mn—Ni-based alloy.

2. The hydrogen sensor according to claim 1, wherein a volume ratio of the Mg—Ni-based alloy to the Zr—Ti-based alloy is 10:0.5 to 10:2.0.

3. The hydrogen sensor according to claim 2, wherein the second catalyst layer is sandwiched between the light control layer and the substrate.

4. The hydrogen sensor according to claim 2, wherein the second catalyst layer is sandwiched between the light control layer and the first catalyst layer.

5. The hydrogen sensor according to claim 2, wherein the second catalyst layer is sandwiched between the light control layer and the first catalyst layer and between the light control layer and the substrate.

* * * * *